(12) United States Patent
Montgomery et al.

(10) Patent No.: US 9,278,111 B2
(45) Date of Patent: *Mar. 8, 2016

(54) METHOD AND APPARATUS FOR GENERATING NITRIC OXIDE FOR MEDICAL USE

(71) Applicant: INO Therapeutics LLC, Hampton, NJ (US)

(72) Inventors: Frederick J. Montgomery, Sun Prairie, WI (US); Duncan P. Bathe, Fitchburg, WI (US)

(73) Assignee: INO Therapeutics LLC, Hampton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,664

(22) Filed: Jun. 18, 2014

(65) Prior Publication Data

US 2014/0363525 A1 Dec. 11, 2014

Related U.S. Application Data

(63) Continuation of application No. 11/355,670, filed on Feb. 16, 2006, now Pat. No. 8,790,715.

(51) Int. Cl.
*A61K 33/00* (2006.01)
*A61M 16/10* (2006.01)
*A61M 16/00* (2006.01)

(52) U.S. Cl.
CPC ............... *A61K 33/00* (2013.01); *A61M 16/10* (2013.01); *A61M 16/107* (2014.02); *A61M 2016/0021* (2013.01); *A61M 2016/0039* (2013.01); *A61M 2016/102* (2013.01); *A61M 2202/0275* (2013.01)

(58) Field of Classification Search
CPC .... A63K 33/00; A61M 16/10; A61M 16/107; A61M 2016/0021; A61M 2016/0039; A61M 2016/102; A61M 2016/107; A61M 2202/0275
See application file for complete search history.

(56) References Cited

U.S. PATENT DOCUMENTS

| | | |
|---|---|---|
| 5,396,882 A | 3/1995 | Zapol et al. |
| 5,485,827 A | 1/1996 | Zapol et al. |
| 5,558,083 A | 9/1996 | Bathe et al. |
| 5,648,101 A | 7/1997 | Tawashi |
| 5,670,127 A | 9/1997 | Sheu |
| 5,827,420 A | 10/1998 | Shirazi et al. |
| 6,089,229 A | 7/2000 | Bathe et al. |
| 6,103,275 A | 8/2000 | Seitz et al. |
| 6,109,260 A | 8/2000 | Bathe |
| 6,125,846 A | 10/2000 | Bathe et al. |
| 6,164,276 A | 12/2000 | Bathe et al. |
| 6,296,827 B1 | 10/2001 | Castor et al. |
| 6,432,077 B1 | 8/2002 | Stenzler et al. |
| 6,474,333 B1 | 11/2002 | Heinonen |
| 6,601,580 B1 | 8/2003 | Bloch et al. |
| 6,749,834 B2 | 6/2004 | Fein et al. |
| 6,758,214 B2 | 7/2004 | Fine et al. |
| 7,025,869 B2 | 4/2006 | Fine et al. |
| 7,040,313 B2 | 5/2006 | Fine et al. |
| 7,220,393 B2 | 5/2007 | Miller et al. |
| 7,560,076 B2 | 7/2009 | Rounbehler et al. |
| 2002/0185126 A1 | 12/2002 | Krebs |
| 2004/0131703 A1 | 7/2004 | Bach et al. |
| 2004/0197274 A1 | 10/2004 | Fein et al. |
| 2005/0036949 A1 | 2/2005 | Tucker et al. |
| 2007/0274874 A1 | 11/2007 | Miller et al. |

FOREIGN PATENT DOCUMENTS

| | | |
|---|---|---|
| CA | 2459891 | 3/2003 |
| EP | 0763500 | 3/1997 |
| EP | 0719159 | 5/1997 |
| EP | 0834332 | 4/1998 |
| WO | WO-03/020211 | 3/2003 |

OTHER PUBLICATIONS

Final Office Action in U.S. Appl. No. 11/355,670, dated Nov. 18, 2013, 15 pages.
Final Office Action in U.S. Appl. No. 11/355,670, dated Jan. 22, 2010, 8 pages.
Non-Final Office Action in U.S. Appl. No. 11/355,670, dated May 7, 2013, 13 pages.
Non-Final Office Action in U.S. Appl. No. 11/355,670, dated Mar. 9, 2009, 9 pages.
PCT International Search Report and Written Opinion in PCT/US07/02228, mailed Oct. 1, 2007, 9 pages.
Supplemental European Search Report in EP 08870651.2, dated Feb. 22, 2012, 6 pages.

*Primary Examiner* — John Pak
*Assistant Examiner* — Nathan W Schlientz
(74) *Attorney, Agent, or Firm* — Joseph Casino; Wiggin and Dana LLP

(57) ABSTRACT

A method and system for generating and delivering nitric oxide directly to a patient. A reaction chamber is provided that is located at or in close proximity to the patient and reactants within the reaction chamber react together to produce a predetermined amount of nitric oxide. The reaction is controlled by metering at least one of the reactants into the reaction chamber to generate a predetermined quantity of nitric oxide as required by the patient. The reactants can include a nitrite salt, such as sodium nitrite, and a reductant such as ascorbic acid, maleic acid or a mixture thereof. By generating and delivering the nitric oxide directly to the patient in close proximity thereto, the formation of $NO_2$ is minimized. One or both of the reactants may be in liquid form.

20 Claims, 8 Drawing Sheets

Figure 1 Liquid Nitrite on to a solid reductant
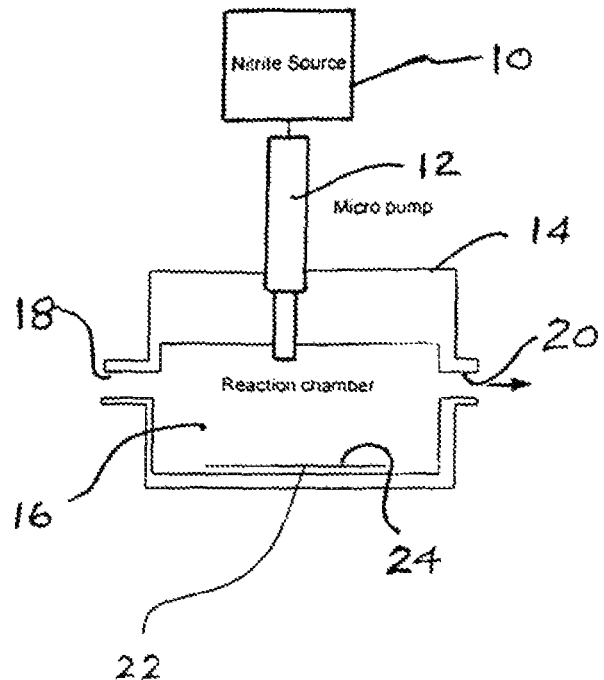
Figure 2 Liquid Nitrite onto a Solid Reductant on a Tape Advance Mechanism
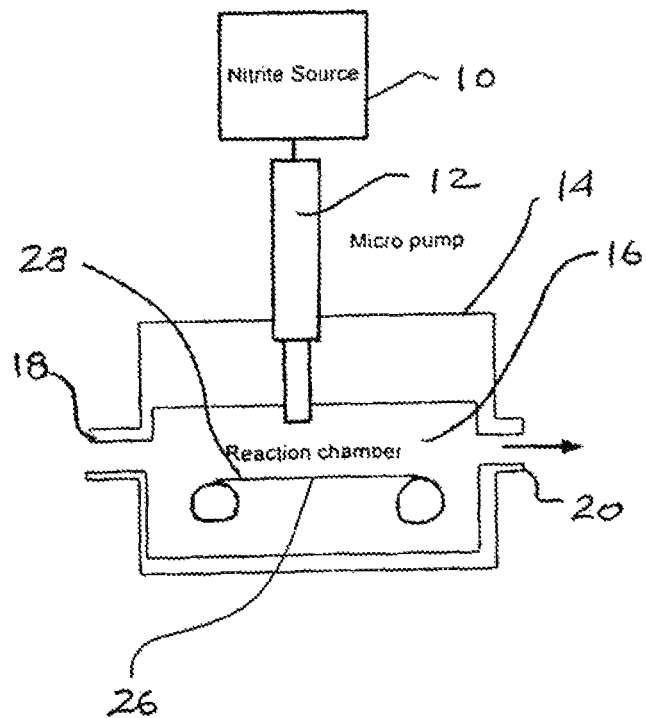

Figure 3 Aqueous Sodium Nitrite into Liquid Reductant
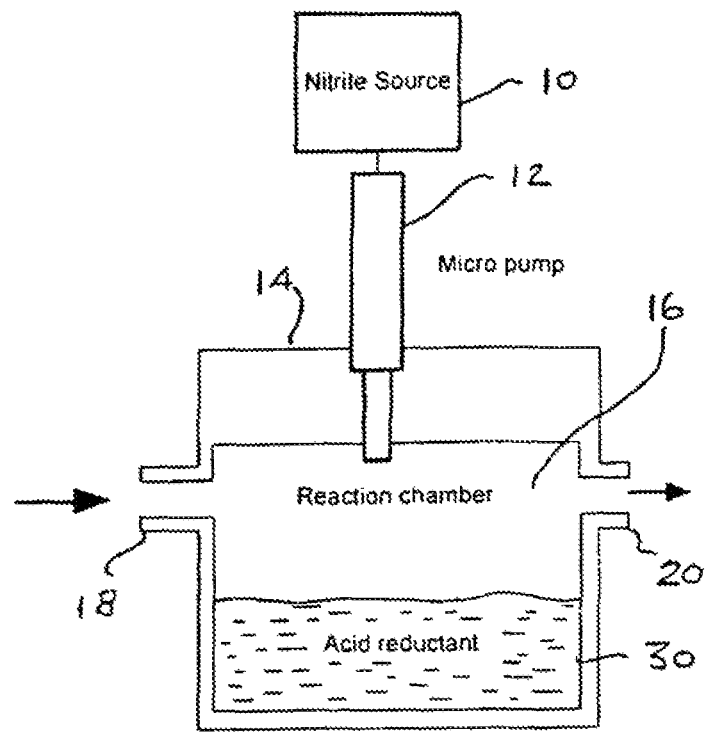
Figure 4 Aqueous Sodium Nitrite into Liquid Reductant on a rotary surface.
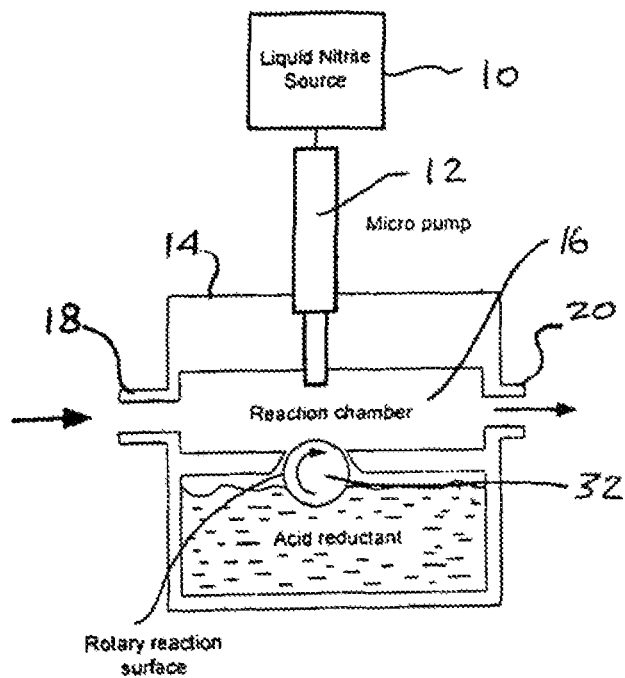

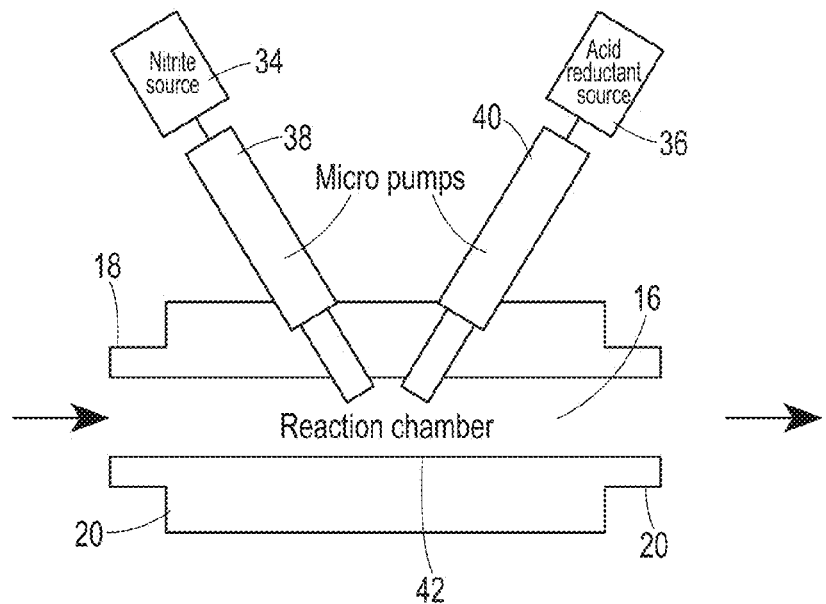
Figure 5. Liquid Nitrite and Liquid Reductant dispensed on to Reaction Surface
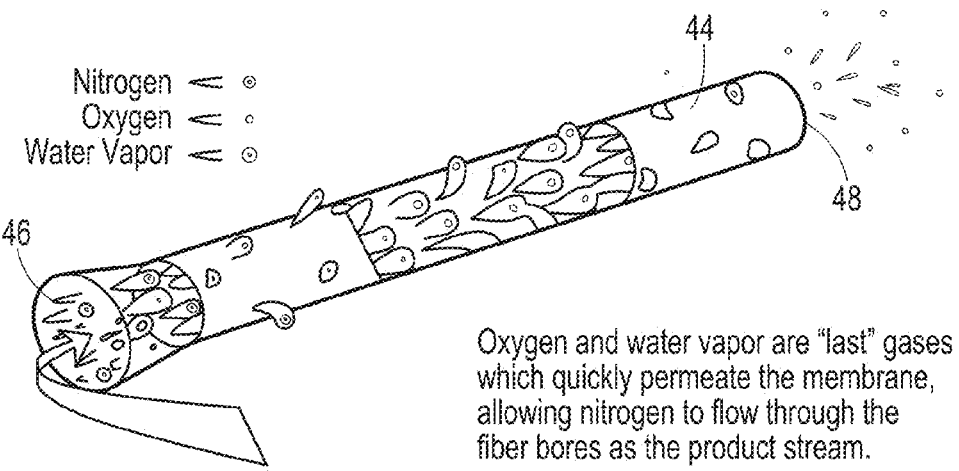
Figure 6. Membrane Filtration to Reduce Oxygen levels in Chamber Gas.

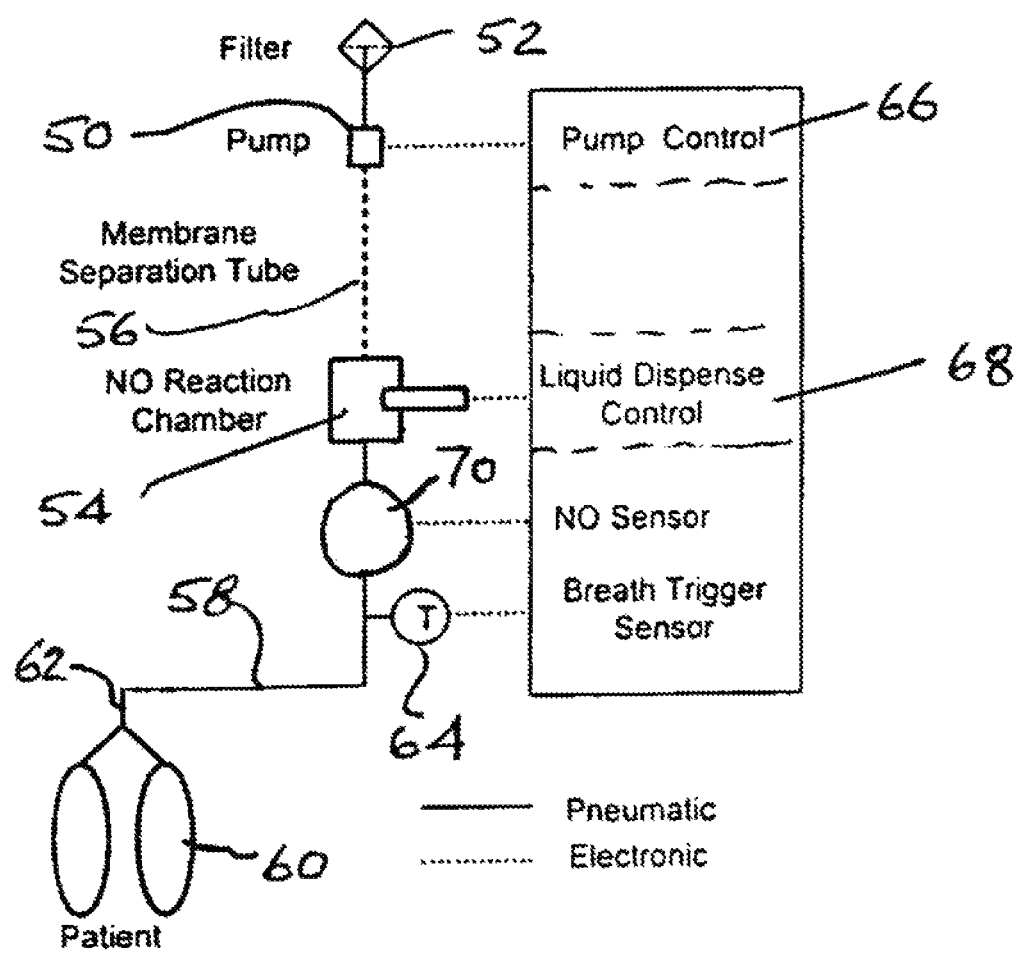
Figure 7 NO Delivery to a Spontaneous Breathing Patient

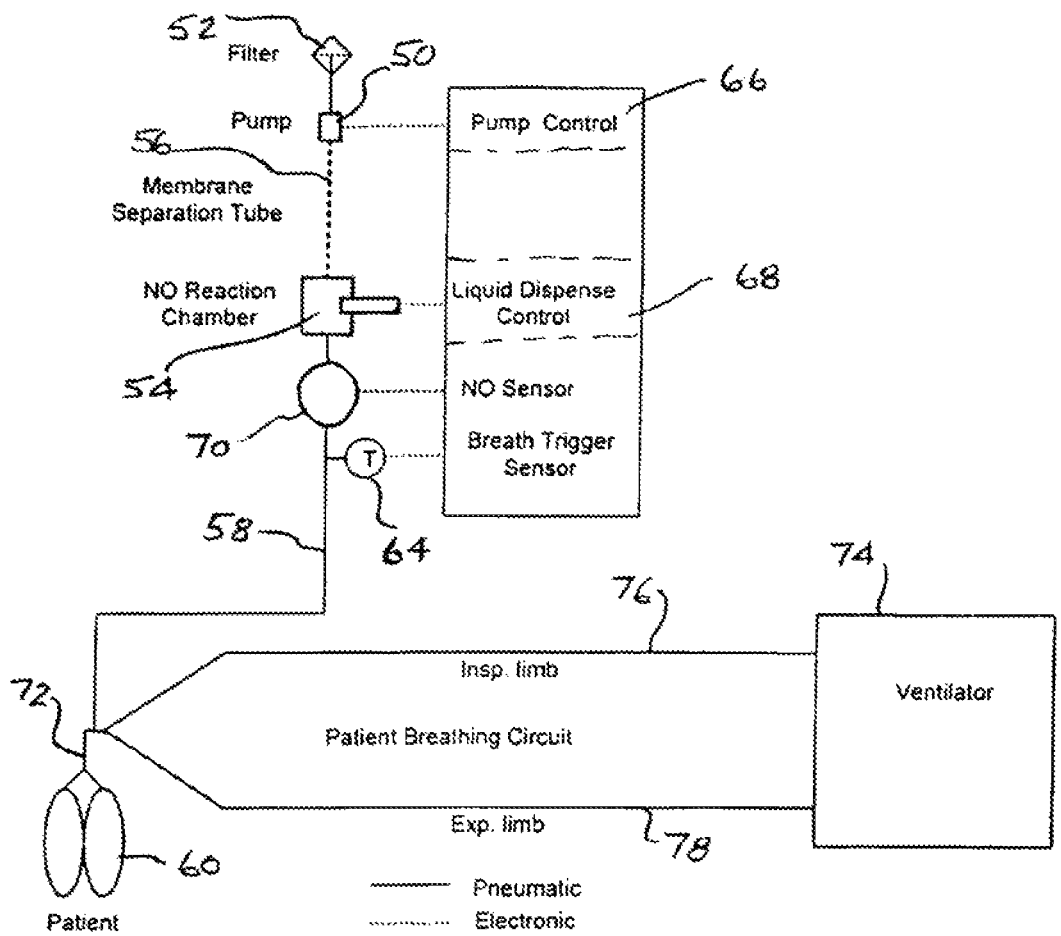

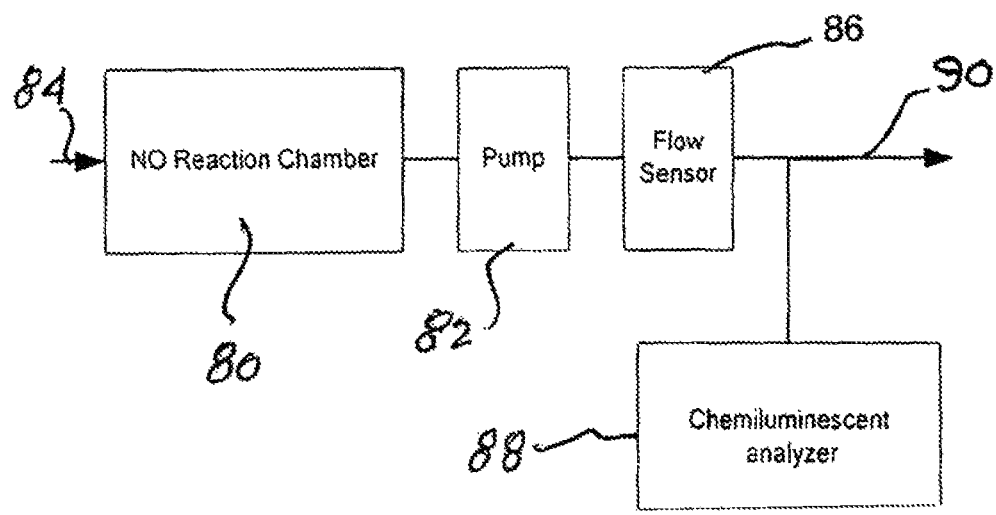
Figure 9 Test set up for monitoring NO output from the NO Generation Chambers.

METHOD AND APPARATUS FOR GENERATING NITRIC OXIDE FOR MEDICAL USE

CROSS-REFERENCE TO RELATED APPLICATIONS

This application is a continuation of U.S. patent application Ser. No. 11/355,670 filed Feb. 16, 2006, now allowed, the disclosure of which is hereby incorporated by reference in its entirety.

FIELD OF THE INVENTION

The present invention relates to a method and system for generating and administering nitric oxide (NO) to a patient, and, more particularly, to a method and system that generates the NO proximate to and for immediate delivery to the patient.

BACKGROUND OF THE INVENTION

The administration of nitric oxide (NO) gas via inhalation for treating patients with pulmonary hypertension is described in Zapol and Frostell's U.S. Pat. No. 5,485,827 "Methods and Devices for Treating Pulmonary Vasoconstriction and Asthma".

At the present, nitric oxide gas is commonly used for the treatment of persistent pulmonary hypertension in the newborn and is indicated for the treatment of term and near-term (>34 weeks) neonates with hypoxic respiratory failure (HRF) associated with clinical or echocardiographic evidence of pulmonary hypertension. In babies with HRF, blood vessels in the lungs constrict, making it difficult for the heart to pump blood through the lungs for oxygenation. Nitric oxide is a pulmonary vasodilator, which relaxes the blood vessels of the lungs in newborns whose heart and lungs could not otherwise carry enough oxygenated blood to the body tissues.

There are also other clinical applications in which NO is used to treat surface infections on the skin of a patient as described in U.S. Pat. No. 6,432,077.

U.S. Pat. No. 5,670,127 "Process for the Manufacture of Nitric Oxide" (Lien-Lung Sheu) describes a method for producing nitric oxide, NO, for medical use by reacting aqueous nitric acid with gaseous sulfur dioxide in a gas-liquid contact reactor to produce 100% NO gas. It is important to note that all of the reactants used in this method are hazardous to handle and, accordingly, the process has to be strictly controlled. The NO produced by this method, which is close to 100%, is blended with an inert diluent, preferably nitrogen, to produce a pressurized gas source in a safe and useable concentration, currently in the range of 100 to 800 ppm of NO. Because this method uses cylinder concentrations in the parts per million (ppm) level it requires the use of large pressurized cylinders (approximately 175 mm diameter and 910 mm high with a wetted volume of 16 L and a weight of 18 Kg), which are bulky, heavy, and provide logistical problems and safety requirements associated with the handling of large pressurized gas cylinders. The cylinders are pressurized to 150 Bar and hold approximately 2000 L of useable gas. However, at a concentration of 800 ppm NO gas, the total drug quantity is 0.066 moles which weighs only 2 gms. Hence, it can be seen that the drug packaging represents 9,000 times the weight of the drug contained therein.

Nitric oxide readily combines with oxygen ($O_2$) to form nitrogen dioxide ($NO_2$), a known toxic gas, so it is very important that the gas cylinder does not become contaminated with oxygen. It is for this reason that the diluent gas used in the cylinders is one that is inert to, i.e. will not oxidize, nitric oxide. While a number of such inert gases are known, it is preferred to utilize nitrogen, $N_2$, primarily on the basis of cost.

The delivery apparatus for dispensing gaseous NO has to deliver the NO source gas into the patient's respirable gas to give a concentration in the range of 1-80 ppm to the patient's lung in a precise and controllable manner. It also has to deliver it in a manner that minimizes the formation of $NO_2$. The parameters that are relevant to the formation of $NO_2$ are the square of the NO concentration, the $O_2$ concentration and the time for the reaction between them to take place. The $O_2$ concentration is not normally controllable by the NO delivery device and the source gas is at a fixed concentration, therefore, the time for the reaction to take place is the only variable.

Apparatus for the delivery of nitric oxide (NO) from a gas cylinder has to not only precisely deliver the correct dose of NO to the patient, but also to minimize the time from delivery to when the patient breathes in the gas to prevent the formation of $NO_2$ at unsafe levels. An example of a bedside NO delivery device that achieves these two functions is described in U.S. Pat. No. 5,558,083 which shows how a constant concentration of NO can be delivered to a patient who is on a gas delivery system such as a ventilator. Smaller ambulatory NO delivery devices are described in U.S. Pat. Nos. 6,089,229, 6,109,260, 6,125,846, and 6,164,276, which describe how dosing can be provided in a pulse mode while keeping $NO_2$ levels at an acceptably low level. While these pulse devices allow a compact and low weight delivery device to be made, they still require the bulk and weight of the NO cylinder for NO to be delivered.

Because of the challenges surrounding the current method of producing, distributing and safely administrating nitric oxide from pressurized cylinders to a patient, there have been a number of alternate solutions proposed to generate NO locally and to immediately deliver it to the patient. Some of those alternate solutions include using an electric arc discharge to produce NO from air prior to delivering it to a patient (U.S. Pat. No. 5,396,882): producing NO for inhalation by establishing a coulometric reduction of copper ions in a solution of nitric acid along with purging the chamber with an inert gas (U.S. Pat. No. 5,827,420); using a corona discharge to generate NO in a chamber that contains oxygen and nitrogen (EP 0719159); using a plasma chemical reaction method while heating the reaction chamber to 400-800° C. to obtain high efficiency of NO production (U.S. Pat. No. 6,296,827); and using heat to break down an organic nitrogen-containing compound, such as ammonia, to form NO (U.S. Pat. No. 6,758,214).

Each of the proposed solutions, however, has certain drawbacks in the generation of NO for direct delivery to the patient rather than having to handle the bulk and weight of pressurized gas cylinders and all of the proposed solutions fall to meet at least one of the requirements for a successful portable and safe NO generation system for the immediate delivery of NO to a patient. These requirements can include (1) compact size for easy handling (<100 mm×150 mm×50 mm); (2) low weight for easy portability (<2 Kgs), (3) no toxic compounds or byproducts that would raise safety concerns, (3) any reactants used should be readily available and not have any special storage or handling requirements, (4) low electrical power consumption so that battery operation is possible if necessary, (5) accurate, controllable generation of NO in just the amount needed for the patient and (6) fast generation so NO can be made and delivered to a patient without allowing $NO_2$ to form.

Accordingly, it would be advantageous to have a method and device for the local generation of NO for immediate delivery to the patient and which overcomes the drawbacks and difficulties of the prior attempted solutions and which also possesses all of the desirable characteristics of such a system.

SUMMARY OF THE INVENTION

This invention describes methods and devices for the local generation of NO for immediate delivery to a patient that is compact, low weight, requires no toxic reactant compounds, uses low electrical power and provides fast and controllable NO generation. A general aspect of the invention is a method for producing nitric oxide (NO) for the immediate delivery to a mammal, i.e. human or animal by bringing together controllable quantities of a nitrite salt, preferably sodium nitrite, and a reductant, preferably at least one of ascorbic acid and maleic acid, in the presence of water in the desired quantities to produce the amount of NO required by the mammal and for the NO to then be immediately delivered to the mammal. Preferably, NO produced in accordance with the present invention is delivered for inhalation by the mammal. By generating the NO within the apparatus immediately prior to delivering it to the mammal, the time for $NO_2$ formation is kept to a minimum. These and other features and advantages of the present invention will become more readily apparent during the following detailed description taken in conjunction with the drawings herein.

BRIEF DESCRIPTION OF THE DRAWINGS

FIG. 1 is a schematic view of a device that can be used for carrying out the present invention, FIG. 2 is a schematic view of an alternative device that can be used for carrying out the present invention, FIG. 3 is a schematic view of another alternative device that can be used for carrying out the present invention, FIG. 4 is a schematic view of a still further alternative device that can be used for carrying out the present invention, FIG. 5 is a schematic view of yet another alternative device that can be used for carrying out the present invention, FIG. 6 is a perspective view of a membrane separation tube usable with the present invention, FIG. 7 is a schematic view of a system for using the present invention with a spontaneously breathing patient, FIG. 8 is a schematic view of a system for using the present invention with a mechanically ventilated patient, FIG. 9 is a schematic view of a test set up for carrying out testing of the present invention.

DETAILED DESCRIPTION OF THE INVENTION

Figure 10:
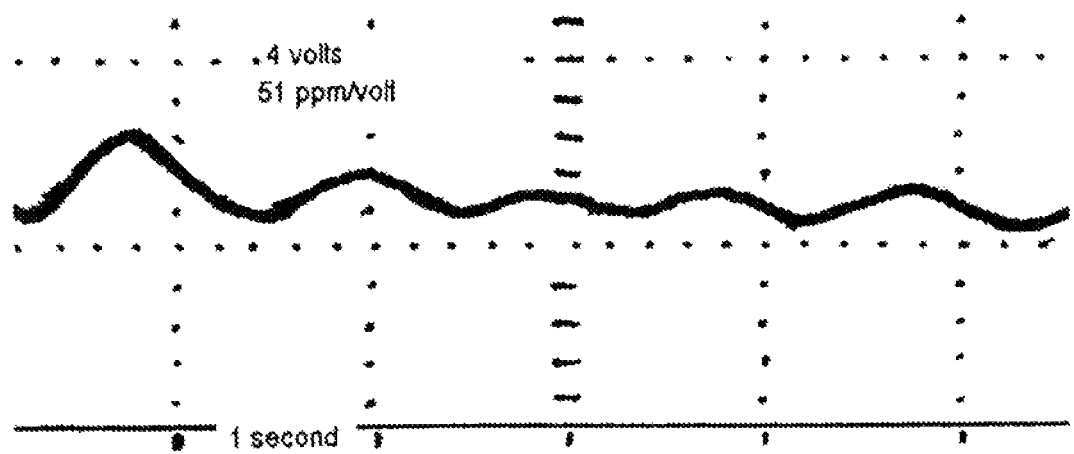
FIG. 10 is an illustration of the test results for NO concentrations for Example 1 using the present invention.

The present invention uses a nitrite and a reductant in the presence of water to generate NO in gaseous form. In an exemplary embodiment, the nitrite source is sodium nitrite and the reductant is at least one of ascorbic acid and maleic acid, preferably ascorbic acid. The use of these exemplary reactants assures that the materials used to produce the NO are both non-toxic; that is, ascorbic acid is Vitamin C and sodium nitrite is used in curing meats, such as ham, and the like. Therefore, the reactant compounds can be used in proximity to the patient without the danger of toxic materials passing downstream to ultimately reach the patient. As used herein, the term "patient" refers to a human or an animal, preferably the former. In addition, all the reactant compounds are soluble in water, therefore, solutions containing equimolar quantities thereof can readily be prepared The reaction that produces NO when generated by sodium nitrite and ascorbic acid in accordance with the present invention can be illustrated by Equation 1

$$2NaNO_2 + 2C_6H_8O_6 \Rightarrow 2NO + 2NaC_6H_7O_6 + H_2O + \tfrac{1}{2}O_2 \quad \text{Equation 1}$$

The reactant compounds used to generate NO according to Equation 1 are widely used in the food industry and are non-toxic in the quantities contemplated herein as described above.

One embodiment of the invention is an apparatus that uses an aqueous solution of sodium nitrite that is deposited as liquid droplets in a controlled amount onto an molar excess of ascorbic acid (in solid form or as an aqueous solution). Preferably, very fine droplets are utilized, thus enabling the reaction to proceed quickly and the NO thus-formed available for inhalation or application.

The amount of NO provided from the reaction is governed by controlling a precise amount of liquid to be brought into contact with the other reactant or reactants. The liquid being dispensed into the reaction chamber is preferably aqueous solutions of the nitrite and/or the reductant. If both the nitrite and the reductant are in a solid state on a substrate, the liquid dispensed to initiate and control the reaction will be water.

The aqueous solutions utilized to generate NO in accordance with the present invention may contain different molar strengths of sodium nitrite with the size of the liquid reservoir required varying inversely with the molar concentration. For instance, utilizing a 6 molar aqueous solution of sodium nitrite, the amount of solution that would produce the same number of moles of NO as are contained in the 16 L cylinder described above would be just 12 mL and weigh only 12.4 grams. Given a plastic package/housing for the solution (similar to an inkjet printer cartridge), the size would be approximately 30 mm×45 mm×45 mm and weigh around 20 gms, or a total weight of 33 grams. As can be seen compared with the gas cylinder for NO, this gives significant improvement with regard to the drug package size and weight.

To determine the amount of liquid to be dispensed, it is necessary to quantify the amount of NO required by a patient. The typical range of NO concentration being inhaled by a patient to reduce pulmonary hypertension is 5 to 80 ppm of NO. A typical alveolar volume per patient breath is around 300 to 400 mL at rest. The amount of NO required per breath can therefore be calculated from equation 2.

$$N = P \cdot V / (Ru \cdot T) \quad (2)$$

Where:
N is the number of moles of the gas (mole)
P is the absolute pressure of the gas (joule/m3)
V is the volume of the particular gas (m3)
Ru is the universal gas constant, 8.315 (joule/(gmole·° K)
T is the absolute temperature (° K)

Assuming atmospheric pressure (101,315 joule/m3) and 20° C. (293° K) as the temperature and expressing the volume in mL (×10⁻⁶ m3), equation (2) reduces to:

$$N = 4.16 \times 10^{-5} \cdot V \text{ (moles)} \quad (3)$$

Equation (3) can be used to calculate the number of moles of NO gas to be delivered to a patient's alveolar volume for a specified concentration by using equation (4).

$$N_{NO} = C_{NO} \cdot 10^{-6} \cdot 4.16 \times 10^{-5} \cdot Va \quad (4)$$

Where;

$C_{NO}$ is the concentration of NO (ppm)

Va is the alveolar volume (mL)

For example if the NO concentration required is 5 ppm and the alveolar volume is 300 mL, the amount of NO in moles to be delivered to the patients alveoli per breath would be;

$$N_{NO}=5\times10^{-6} \cdot 4.16\times10^{-5} \cdot 300=250\times10^{-9} \text{ moles or 62 nmoles.}$$

The molecular weight of sodium nitrite is 69. Hence, a one molar solution contains 69 grams of sodium nitrite per liter. Assuming the reaction described above is 100% efficient and all of the NO produced from the nitrite is in gaseous form, one nmole of NO gas will be produced for every nL of a one molar solution of sodium nitrite.

The quantity of liquid needed can be reduced by increasing the strength of the solution. For example, if a 2 molar solution were used, then the amount of liquid needed would be reduced by 50 percent. The amount of liquid can be produced as one droplet of exactly the right size or multiple droplets of a smaller size which add up to the amount needed.

Therefore, it is apparent that it is possible in accordance with the present invention to accurately control the formation of the NO in order to treat the individual patient with specific regard to the desired concentration of the NO to be delivered and the alveolar volume of the patient.

The bringing together of the two reacting compounds can be achieved in a number of ways. Preferably, a reactant in aqueous solution can be delivered by a suitable liquid dispensing means to the other reactant, which may be in liquid or solid form. In another embodiment, both the nitrite salt and the reductant are in solid form on a substrate and controlled amounts of water are dispensed onto the substrate to allow a controlled amount of the reactants to react thereby generating a controlled amount of NO.

Turning to FIG. 1, there is shown a schematic view of a system that can be used where one of the reactants is utilized as an aqueous solution and the other is a solid. In the exemplary embodiment of FIG. 1, there can be seen a liquid reactant source 10 that can be an aqueous solution of a nitrite salt. The liquid nitrite from the source 10 is withdrawn or pumped out by a liquid dispensing means in the form of a controllable micro pump 12 so that the liquid nitrite enters a housing 14 enclosing a reaction chamber 16. The housing 14 also has formed therein an inlet 18 for admitting room air or other carrier gas and an outlet 20 for discharging the NO-laden carrier gas from the reaction chamber 16 to deliver that gas to a patient. The liquid dispensing means or micro pump 12 can be constructed through a number of different technologies that could be used to dispense nanoliter amounts of liquid.

One possible technology can involve individual micro pump valves which open for a short period of time and allow liquid from a pressurize reservoir to be delivered through a small orifice (0.1 to 0.25 mm diameter) while in the open phase. Another technology for the micro pump 12 can be through the use of inkjet style printer heads (piezoelectric or thermal) to deliver the fine droplets required. Typical inkjet printer heads have droplet sizes of 10 to 100 picoliters (100× $10^{-12}$ L) which is substantially smaller than would be required in the practice of the present invention. However, such ink jet printer heads can have up to 100 orifices per printhead and can deliver droplets at a rate of up to 12 MHz. Accordingly, by delivering multiple droplets from multiple orifices, the total amount required can be delivered very quickly. For instance, 100 orifices delivering simultaneously 6 droplets/orifice would be needed to deliver the 62 nL in the example above.

A disk 22 of substrate material, such as polyethylene, has a thin layer of the other reactant, i.e. the reductant, coated on a reaction surface, that is, the upper surface 24 thereof such that the liquid nitrite droplets hit the coating of the reductant on the upper surface 24 of the disc 22 to allow the reaction to take place as has been previously explained, thereby forming NO gas that then passes through the outlet 20 to enter the airway of the patient. In order to continue the process, the disc 22 can be rotated to advance to a new position after each local reaction from a droplet, and the position of the micro pump 12 can move along a linear path from the outside of the disc 22 to the inside to create a spiral thereby using all of the available reactant that is present on the upper surface 24 of the disc 22. As can be seen, the reaction is controlled by the rate the reactant liquid is caused to enter into the reaction chamber 16 and contact the solid reactant.

In FIG. 2 there is shown a schematic view of an alternate embodiment where a liquid reactant is contacted with a solid reactant. In the embodiment shown in FIG. 2, the basic components are the same and have been give the same identification numbers, however, in this embodiment, the reaction takes place on a tape 26 that is movable. As such, as each droplet falls from the micro pump 12, it hits the thin layer of the other reactant that is coated to the upper surface 28 of the tape 26 where the reaction takes place. After each droplet reacts, the tape 26 can be moved to provide another area of the solid reactant coating to receive a subsequent droplet. If the tape 26 is wide, the position of the micro pump 12 can move along a lateral linear path that is at a right angle to the direction of the movement of the tape 26, to use all the available reactant that is present on the upper surface 28 of the tape 26.

Turning now to FIG. 3, there is shown a schematic view of a system wherein both of the reactants are present in liquid form with, again, only a single liquid dispensing means being utilized. Thus, in FIG. 3, there can be seen a liquid reactant source 10 that can be liquid nitrite compound, such as an aqueous solution of sodium nitrite. Again, the liquid nitrite from the source 10 is withdrawn or pumped out by a liquid dispensing means in the form of a controllable micro pump 12, so that the liquid nitrite enters a housing 14 enclosing the reaction chamber 16. In this embodiment, however, the other reactant, i.e. the reductant, is in liquid form and is located in a reservoir 30 formed in the housing 14.

The droplet of the nitrite thereupon falls from the micro pump 12 down into the liquid reductant, so as to react therewith and form the NO gas that is passed through the outlet 20 to the airway of the patient. Since the supply of the liquid reductant is by means of a reservoir, it will be appreciated that there is no need to move the location of the micro pump 12. Again, the reaction that takes place between the reactants, and therefore the production of NO, is controlled by controlling the rate at which the droplets of nitrite are introduced into the reaction chamber 16 to react with the liquid acid reductant since the reaction will take place only so long as there is nitrite salt present to react.

Turning next to FIG. 4, there is an exemplary embodiment of an alternative embodiment to the FIG. 3 embodiment and where there is a roller 32 having an outer surface that is partially disposed below the surface of the liquid reductant such that, as the roller 32 rotates, fresh liquid reductant is continually brought out of the reservoir 30 so as to be positioned to receive a droplet of the liquid nitrite from the micro pump 12. As such, as a droplet of the liquid nitrite hits the upper area of the outer surface of the roller 32 to react with the liquid reductant located thereon, the roller 32 can be rotated to bring a fresh supply of the liquid reductant in position to receive the next droplet. To speed up the reaction, the outer surface of the roller 32 can be roughened to increase the local surface area.

Turning to FIG. 5, there is shown a schematic view of a system where both of the reactants are in aqueous solution and there is a pair of liquid dispensing means. As can be seen, therefore, there is a nitrite source 34 and a reductant source 36, both of which have their respective liquids removed therefrom by means of micro pumps 38 and 40. The respective droplets are then dispensed onto a reaction surface 42 within the reaction chamber 16. There is a movement system by which the reaction surface 42 is moved to assure that the two droplets are deposited at the same location on the reaction surface 42 so that the individual droplets of reactants can react with each other. The movement system can move either the micro pumps 38 and 40 or the reaction surface 42, or both, to make sure there is a proper alignment of the respective droplets to provide the reaction for producing NO.

As examples of such movement system, the reaction surface 42 can be a rotating disc, a rotating cylinder or a tape advancement mechanism, each of which are described with respect to FIGS. 2-4, and which can be used to align or register the location of the second deposited droplet with the first deposited droplet. In addition, the surface of the index substrate can be heated to increase the reaction rate and to cause any residual water to be evaporated.

In any of the foregoing devices or systems, after the NO has been generated, the remaining reaction side product, e.g. sodium ascorbate, has to be removed from the liquid dispensing means so as to not interfere with following reactions. Some of the solutions described above have inherent means in the design to do this; for example, in the FIG. 2 embodiment, as the tape 26 is advanced to its next index position, it automatically removes the side product compound from the liquid dispensing means and stores it on the tape 26. Similarly, as the roller 32 of the FIG. 4 embodiment rotates to bring a new supply of the liquid reactant to the upper area, that movement also removes the side product compound from the reaction surface.

However in the embodiment of FIG. 5, where both of the liquid reactants are dispensed in a controlled manner, some way of removing the side products must be added. This could be a rotating cylinder that is heated to dry the side product into a solid form where it can be scraped off into a holding chamber below the cylinder. This holding chamber can also have neutralizing compounds, such as activated charcoal, to stop any further reaction and to keep any cross-over from the holding chamber getting back into the reaction chamber. Another way of achieving this is to have the holding chamber at a lower pressure by pumping gas out of it and passing it through a scrubber before exhausting to atmosphere.

As stated, there can be a problem with the build up of $NO_2$ levels since that compound is toxic and therefore must be prevented from being generated and administered with the NO to a patient. To that end, a number of solutions can be employed. One such solution is to construct the reaction chamber to be extremely small so as to reduce the washout time and be designed with no areas that can allow stagnant gas to accumulate and cause $NO_2$ to form.

Another solution is to provide the gas flow through the reaction chamber to be low in oxygen in order to reduce the $NO_2$ reaction rate. This can be achieved with membrane separation technology (FIG. 6) which preferentially allows oxygen and water vapor to pass out of the gas stream prior to the reaction chamber. As can be seen in FIG. 6, therefore, there is a membrane separation tube 44 though which the gas passes to be fed into the NO generating device of the present invention. Thus, as the air is moved from the inlet 46 to the outlet 48 of membrane separation tube 44, the water vapor and oxygen, being "fast gases", quickly permeate through the wall of the membrane separation tube 44 and allow the nitrogen to pass through the bore of the membrane to be supplied for the NO reaction of the present invention.

As a further solution, the $NO_2$ can be removed downstream of the chamber with the addition of an $NO_2$ scrubber. Materials that can be used to remove $NO_2$ are sulfurous polymer (see EU 0763500A2) or soda lime.

There are a number of systems by which the present invention can administer the NO generated to the patient. The simplest means is for the patient to breath in through the reaction chamber so the NO generated is taken directly into the patients lung like an inhaler. The patient would simply press a button to generate the NO and then inhale the gas mixture directly from the reaction chamber.

Rather than have the patient press a button, the device could have sensor means to detect when the patient took a breath and that would signal the device to generate the NO. This detection of the patient's inspiration could be either by pressure drop or flow indication.

Instead of a simple inhaler with the reaction chamber proximal to the patient, there is shown, in FIG. 7, a gas delivery system for a spontaneously breathing patient that has a pump 50 that draws in room air through a filter 52 and pumps that air through the reaction chamber 54. There may also be a membrane separation tube 56 located upstream of the reaction chamber 54 to remove some oxygen in the manner and for the purpose as explained with respect to the membrane separation tube 44 of FIG. 6. It should be noted that while the pump 50 is shown located upstream of the reaction chamber 54, it could alternatively be located downstream of the reaction chamber 54 and draw the air through the reaction chamber 54.

A conduit 58 delivers the NO-containing gas from the reaction chamber 54 to the patient 60 where it can be administered to the patient 60 by means of a patient device such as a nasal cannula 62. A nasal cannula is designed to provide supplemental air flow to the patient and therefore, does not form a seal with the patient's airway, so additional room air is taken in as the patient breathes. The conduit 58 could also contain a breath trigger sensor 64 to act as a breath detector to determine when the patient was breathing in and, therefore, when to generate the NO. The pump 50 could operate either continuously or only when NO was being generated and hence work in a pulse mode to deliver gas flow through the reaction chamber 54 where the stream of gas picks up the NO and carries it through the nasal cannula 62 and thence to the patient 60. As such, there may be a pump control 66 that controls the operation of the pump 50. In addition, there is a liquid dispense control 68 that controls the reaction occurring within the reaction chamber 54 as has been previously explained so that the amount of NO generated is controlled to provide the desired amount of NO to the patient 60. As also can be seen, there is a NO sensor 70 in the conduit 58 to determine the concentration of NO leaving the reaction chamber 54.

Turning next to FIG. 8, there is a schematic view of a NO delivery system for use when the patient is being mechanically ventilated. As can be seen in FIG. 8, there is, again, a pump 50 that draws in room air through a filter 52 and pumps that air through the reaction chamber 54 with an optional membrane separation tube 56 located upstream of the reaction chamber 54. Conduit 58 delivers the NO containing gas from the reaction chamber 54 where it can be administered to the patient 60. This conduit 58 could also contain a breath trigger sensor 64 that senses the breathing of a patient and a pump control 66 that can be utilized as described with respect to FIG. 7. There is also a liquid dispense control 68 that controls the reaction occurring within the reaction chamber 54 as has been previously explained so that the amount of NO generated is controlled to provide the desired concentration of NO to the patient 60. In this embodiment, however, instead of a nasal cannula, the patient device can be a endrotracheal tube or face mask 72 that interjects the NO-containing gas along with the gas administered by ventilator 74 through the inspiratory limb 76. The expired gases from the patient 60 are carried from the patient 60 through the expiratory limb 78 back to the ventilator 74. As before, a NO sensor 70 is present to determine the concentration of NO in the stream of gas delivered to the patient 60. As will be appreciated, other gas delivery systems can be used in place of a ventilator, such as a breathing bag filled with gas from a flowmeter, or a constant positive airway pressure (CPAP) where the gas flow is from a blower.

Examples of NO Generation Chamber Designs

The following examples describe different configurations of reaction chamber design which use different sources of reaction compounds (both solid and liquid) to generate NO. The test configuration in each case was as described in FIG. 9 and which includes a reaction chamber 80 where the reaction takes place in generating the NO. A pump 82 continuously pulls in room air via an inlet 84 so as to pass through the reaction chamber 82 where the reaction takes place in the generation of NO. A flow sensor 86 is located downstream of the reaction chamber 80 that measures the total gas flow and a chemiluminescent analyzer 88 carries out the analysis of the NO in the gas passing from the outlet 90. The chemiluminescent analyzer 88 has a response time of 60 msec, so it is fast enough to give a real time measurement although there is a 2 second lag in processing time before the measurement is available to a chart recorder.

In each case the liquid dispensing means was a small pressurized (5 psi) liquid reservoir that fed a VHS micro dispensing valve (The Lee Company) using a spike voltage control circuit. The average amount of liquid dispensed was determined by gravimetric measurement over 45 minutes when pulsing once per second.

EXAMPLE 1

The first example was carried out using the apparatus of FIG. 3. Aqueous sodium nitrite (1 molar solution) was dispensed directly into a chamber with a reservoir of liquid reductant. The reductant was 1 molar solution of ascorbic acid with 1 molar maleic acid added. The flow through the reaction chamber (Qc) was 0.5 L/min of air and the micro pump delivered 48 nL per pulse every second.

Results:

Average concentration of NO from the reaction chamber was approximately 123 ppm as shown in FIG. 10.

The amount of NO being generated can be calculated using Equation 4 where Va is the flow per second in mL given by;

$Va = Qc \cdot 1000/60 = 0.5 \cdot 1000/60 = 8.3$ mL/sec.

$N_{NO} = C_{NO} \cdot 10^{-6} \cdot 4.16 \times 10^{-5} \cdot Va$   Equation 4

$N_{NO} = 123 \cdot 4.16 \cdot 8.3 / 100 = 42.5$ nmoles

The speed of the reaction wasn't that quick with the NO output not showing distinct pulses but blending into a continuous output. During the test, it was noticeable that the reaction was taking place some distance below the surface of the reductant with bubbles of gas being formed and taking some time to reach the surface. This was likely causing a time lag in the output as the NO gas slowly bubbled out of the reductant solution.

EXAMPLE 2

This next example was carried out with the use of the apparatus of FIG. 4 having a chamber design where the rotary cylinder was used to bring a layer of reductant to the top of the chamber where the aqueous sodium nitrite (1 molar solution) was dispensed onto it. This design was to reduce the delay associated with bubbles of NO forming below the surface of the reductant as seen in Example 1. The flow through the chamber was 0.5 L/min of air and in this case the micro pump was delivering 42 nL per pulse. After each pulse, the rotary reaction surface was rotated to bring fresh reductant to the dispensing means. The rotary reaction surface was roughed up with 400 grip sand paper to provide better reductant retention. The reaction chamber size was also reduced in this design to again speed up the response time of the NO output.

Figure 11:
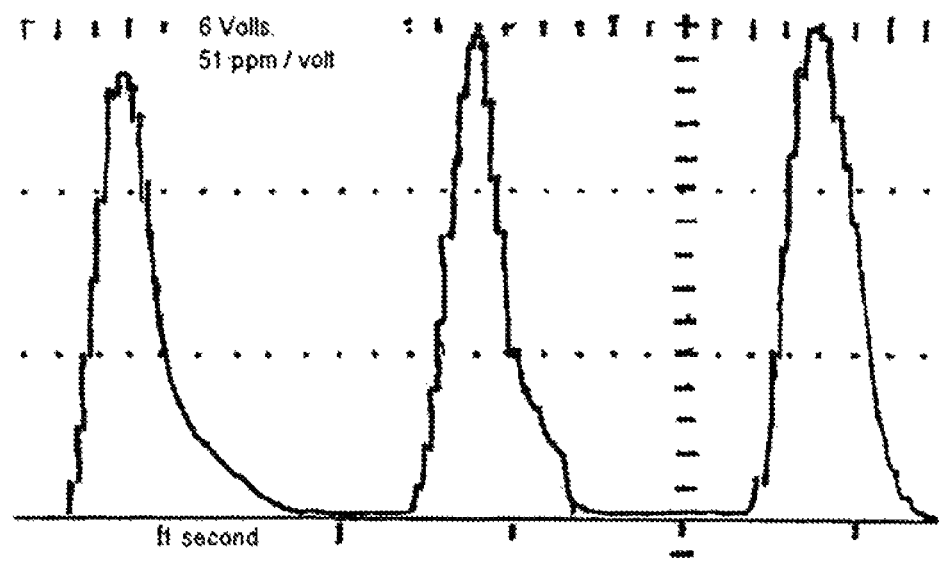
FIG. 11 is an illustration of the test results for NO concentrations for another Example of a use of the invention.

Results:

As can be seen on the chart of FIG. 11, the response time of the reaction was a lot quicker with distinct pulses of NO corresponding to each droplet of sodium nitrite solution being delivered. The total reaction time for each pulse was less than 1 second. The peak NO concentration was approximately 300 ppm, with an average concentration over a 1 second period of around 117 ppm. This corresponds to an output of about 40 nmoles of NO, but as can be seen, in a substantially reduced reaction time.

EXAMPLE 3

In this example, both the nitrite and the reductant were dispensed with micro dispensing valves that were configured to deposit the liquid droplets at the same location at the bottom of the reaction chamber. The apparatus was as described in FIG. 5. In this example, the sodium nitrite was a 2 molar solution and the reductant was 1.5 molar solution of ascorbic acid with 0.5 molar maleic acid. The micro pump delivered 42 nL per pulse of sodium nitrate and the second pump delivered 54 nL per pulse of reductant both were pulsed simultaneously every second. The gas flow through the reaction chamber was 0.360 L/min of air.

Results:

When the system first started up, the output was peaky as in example 2 but as the liquid built up on the reaction chamber floor the output became more like example 1 with the output having a longer reaction time and an average output of NO being delivered. In the slow steady state condition the average output was 385 ppm NO.

Based on a gas flow of 0.36 L/min this represents an NO output of 96 nmoles/pulse.

EXAMPLE 4

In this example, carried out using the apparatus of FIG. 1, liquid sodium nitrite (6 molar solution) was dispensed onto a solid reductant that had been formed by allowing a solution that was 1 molar in ascorbic acid and 1 molar in maleic acid to evaporate onto a polyethylene disc thereby forming a crystallized thin film of reductant.

The gas flow through the chamber was 5 L/min of air.

The micro pump delivered 43 nL per pulse of the 6 molar sodium nitrate.

Results:

The NO output from the reaction chamber resulted in a peak concentration of 216 ppm NO spike which lasted about 1 second and corresponded to an average concentration of 73 ppm over the 1 second period. At a gas flow 5 l/min air this corresponded to a calculated NO delivery per pulse of 252 nmoles/pulse which is very close to the predicted 43 nL×6 molar concentration which equals 258 nmoles of sodium nitrite delivered.

Figure 12:
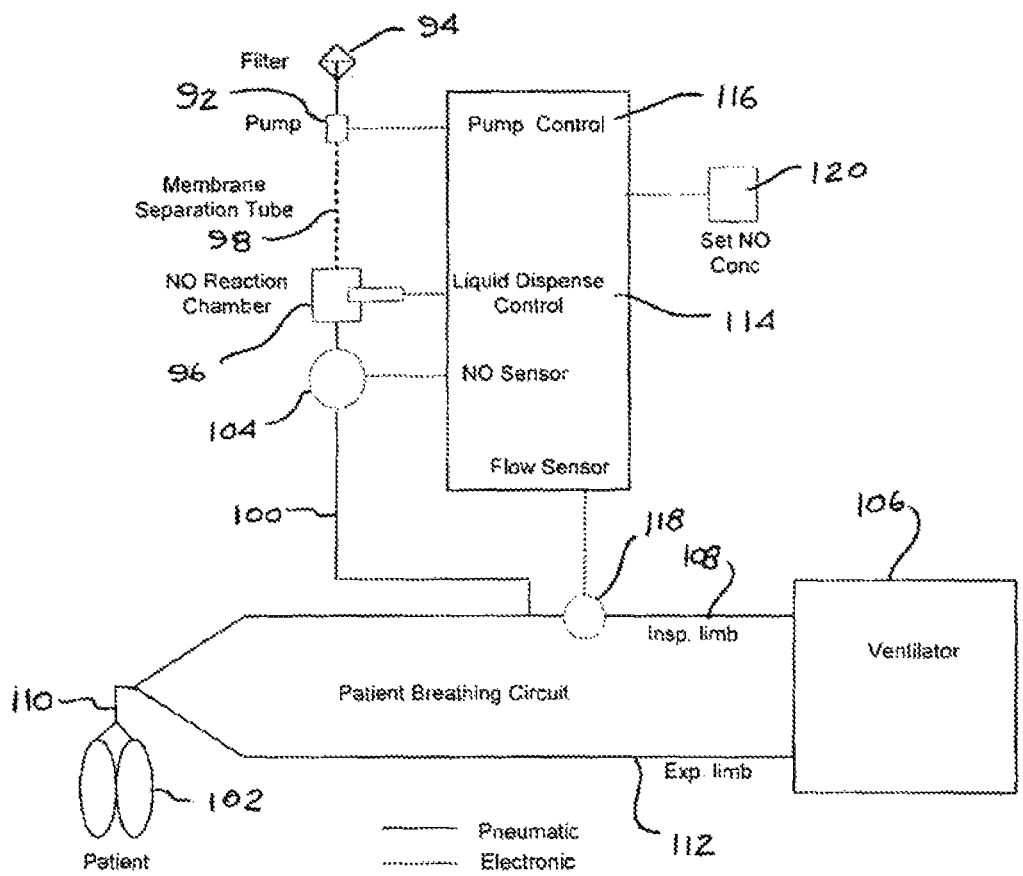
FIG. 12 is a schematic view of a further system for use of the present invention with a NO concentration setting capability.

Turning lastly to FIG. 12, there is a schematic view of a NO delivery system for use wherein the system has the capability of setting the NO concentration to be administrated to a patient. As can be seen in FIG. 12, there is, again, a pump 92 that draws in room air through a filter 94 and pumps that air through the reaction chamber 96 with an optional membrane separation tube 98 located upstream of the reaction chamber 96. Conduit 100 delivers the NO-containing gas from the reaction chamber 96 where it can be administered to the patient 102. There is an NO sensor 104 to determine the concentration of NO in the stream of gas delivered to the patient 102. As with the FIG. 8 system, a ventilator 106 breathes the patient via an inspiratory limb 108 by means of an endotracheal tube or face mask 110 while the exhaled gases from the patient are returned to the ventilator 106 via an expiratory limb 112.

There is also a liquid dispense control 114 that controls the reaction occurring within the reaction chamber 96 so that the amount of NO generated in the NO reaction chamber 96 is controlled and a pump control 116 to control the pump 92. With this embodiment, there is also a flow sensor 118 that is located in the inspiratory limb 108 to measure the flow of the breathing air that is being provided by the ventilator 106 to the patient 102 through that inspiratory limb 108.

In this embodiment, therefore, an input device 120 is provided so that the user can enter the desired concentration of NO to be administered to the patient 102. Since the flow to the patient 102 is known from the flow sensor 118, the liquid dispense control 114 can control the NO being generated in the NO reaction chamber to combine with that known flow to deliver to NO concentration set by the user by the input device 120.

Those skilled in the art will readily recognize numerous adaptations and modifications which can be made to the NO generation system and method of generating NO of the present invention which will result in an improved method and system for generating and directly introducing NO into the airway of a patient, yet all of which will fall within the scope and spirit of the present invention as defined in the following claims. Accordingly, the invention is to be limited only by the following claims and their equivalents.

What is claimed is:

1. A method of controlled delivery of nitric oxide (NO) to the lung of a human patient in need thereof by inhalation comprising:
    delivering droplets comprising nitrite salt dissolved in aqueous droplets to a first position on a moveable reaction surface at a frequency up to 12 MHz, wherein the moveable reaction surface comprises a solid reductant disposed on the moveable reaction surface;
    generating NO through the reaction between the nitrite salt and the reductant;
    moving the reaction surface to a second position;
    delivering droplets comprising nitrite salt dissolved in aqueous droplets to the second position on the moveable reaction surface; and
    controlling the amount of NO delivered to the lung of the patient by controlling the frequency of the droplets delivered to the moveable reaction surface.

2. The method of claim 1, wherein generating NO comprises continuous reaction of the nitrite salt and the reductant.

3. The method of claim 1, wherein controlling the frequency of the droplets delivered to the moveable reaction surface is via a controllable micro pump.

4. The method of claim 1, wherein the NO is delivered at a concentration in the range of 5 ppm to 80 ppm.

5. The method of claim 1, wherein the nitrite salt is sodium nitrite, and, wherein the reductant comprises ascorbic acid, maleic acid or a mixture thereof.

6. The method of claim 5, wherein said reductant comprises a mixture of ascorbic acid and maleic acid.

7. The method of claim 1, wherein the moveable reaction surface is a disc or tape.

8. The method of claim 1, wherein the lung has an alveolar volume in the range of 300 mL to 400 mL at rest.

9. The method of claim 1, wherein the moveable reaction surface is rotatable.

10. The method of claim 1, wherein an amount of NO delivered to the patient is calculated based upon the alveolar volume of the patient and a desired concentration of NO to be delivered to said patient.

11. The method of claim 1, wherein the droplets are delivered at a rate based upon the alveolar volume of the patient and a concentration of NO to be inhaled by the patient.

12. The method of claim 1, wherein generating NO comprises pulsed reaction of the nitrite salt and the reductant.

13. A device for controlled intermittent or continuous delivery of nitric oxide (NO) to the lung of a human patient in need thereof by inhalation, said device comprising:
    a reaction chamber in fluid communication by inhalation with the patient;
    a moveable reaction surface having a reductant disposed thereon; and
    a controllable liquid dispensing system adapted to spray liquid aqueous droplets comprising a dissolved nitrite salt at a controlled continuous or pulsed rate onto the reaction surface to form NO for delivery to the patient by inhalation;
    wherein delivery of NO to the lung is controlled by controlling the frequency of the droplets; and
    wherein the moveable reaction surface is adapted to move to advance to a new position after reaction from the liquid aqueous droplets, thereby delivering the liquid aqueous droplets to reductant disposed on the new position of the moveable reaction surface.

14. The device of claim 13, wherein the droplets have a volume in the range of 10 picoliters to 100 picoliters.

15. The device of claim 13, wherein the frequency is up to 12 MHz.

16. The device of claim 13, wherein the moveable reaction surface is rotatable.

17. The device of claim 13, wherein the wherein the reductant comprises ascorbic acid, maleic acid or a mixture thereof.

18. The device of claim 13, wherein the moveable reaction surface is a disc or tape.

19. A system comprising the device of claim 13 and a ventilator adapted to provide an inspiratory gas to the patient through the device for controlled delivery of NO.

20. The system of claim 19, further comprising an input device adapted to set the desired concentration of NO to be delivered to the patient, and a flow sensor adapted to determine the flow of gas being provided by the ventilator, wherein the amount of NO delivered to the patient is based on the desired concentration entered into the input device.

* * * * *